United States Patent [19]
Fell et al.

[11] Patent Number: 5,769,835
[45] Date of Patent: Jun. 23, 1998

[54] ABSORBENT ARTICLE HAVING TUBULAR, ELASTICIZED BUMPERS

[75] Inventors: David Arthur Fell, Neenah; David Jerome Arteman; Jerry Alan Johnston, both of Appleton, all of Wis.; Phillip Eugene Keck, Alpharetta, Ga.; Lynn Kirkpatrick LeMahieu, Hortonville, Wis.

[73] Assignee: Kimberly-Clark Worldwide, Inc., Neenah, Wis.

[21] Appl. No.: 475,309

[22] Filed: Jun. 7, 1995

[51] Int. Cl.$^6$ .............................. A61F 13/15; A61F 13/20
[52] U.S. Cl. .................................... 604/385.2; 604/385.1
[58] Field of Search ........................ 604/385.2, 385.1, 604/396, 397

[56] References Cited

U.S. PATENT DOCUMENTS

| | | |
|---|---|---|
| 709,223 | 9/1902 | James et al. . |
| 3,081,772 | 3/1963 | Brooks et al. . |
| 3,364,931 | 1/1968 | Hirsch . |
| 3,417,751 | 12/1968 | Murdoch ................................. 604/397 |
| 3,572,342 | 3/1971 | Lindquist et al. . |
| 4,315,508 | 2/1982 | Bolick . |
| 4,451,934 | 6/1984 | Gioello ........................................ 2/113 |
| 4,610,682 | 9/1986 | Kopp .................................... 604/385 R |
| 4,657,539 | 4/1987 | Hasse .................................. 604/385 A |
| 4,663,220 | 5/1987 | Wisneski et al. ........................ 428/221 |
| 4,695,278 | 9/1987 | Lawson ................................ 604/385 A |
| 4,699,823 | 10/1987 | Kellenberger et al. ................. 428/219 |
| 4,704,116 | 11/1987 | Enloe .................................. 604/385 A |
| 4,711,683 | 12/1987 | Merkatoris .............................. 156/164 |
| 4,753,644 | 6/1988 | Cottenden et al. ...................... 604/378 |
| 4,798,603 | 1/1989 | Meyer et al. ............................ 604/378 |
| 4,842,666 | 6/1989 | Werenicz ................................. 156/161 |
| 4,904,251 | 2/1990 | Igaue et al. ........................... 604/385.2 |
| 4,917,696 | 4/1990 | De Jonckheere ..................... 604/385.2 |
| 5,066,527 | 11/1991 | Newell ................................... 428/35.6 |
| 5,133,371 | 7/1992 | Sivess ..................................... 132/212 |
| 5,147,343 | 9/1992 | Kellenberger ........................... 604/368 |
| 5,188,626 | 2/1993 | Toyoda et al. ........................ 604/385.1 |
| 5,188,627 | 2/1993 | Igaue et al. ........................... 604/385.2 |
| 5,192,606 | 3/1993 | Proxmire et al. ........................ 428/284 |
| 5,207,662 | 5/1993 | James ................................... 604/385.2 |
| 5,226,992 | 7/1993 | Morman ................................. 156/62.4 |
| 5,227,107 | 7/1993 | Dickenson et al. ..................... 264/113 |
| 5,295,986 | 3/1994 | Zehner et al. ........................ 604/385.1 |
| 5,336,545 | 8/1994 | Morman ................................... 428/152 |
| 5,364,382 | 11/1994 | Latimer et al. .......................... 604/378 |
| 5,366,453 | 11/1994 | Zehner et al. ........................ 604/385.2 |
| 5,382,246 | 1/1995 | Kawano ............................... 604/385.1 |
| 5,382,400 | 1/1995 | Pike et al. ............................... 264/168 |
| 5,386,595 | 2/1995 | Kuen et al. ................................. 2/400 |
| 5,489,282 | 2/1996 | Zehner et al. ........................ 604/385.1 |
| 5,520,674 | 5/1996 | Lavon et al. .......................... 604/385.2 |
| 5,599,337 | 2/1997 | McCoy ................................. 604/385.1 |

FOREIGN PATENT DOCUMENTS

| | | |
|---|---|---|
| 0 203 712 A1 | 12/1986 | European Pat. Off. . |
| 0217032A3 | 4/1987 | European Pat. Off. . |
| 0 446 867 A2 | 9/1991 | European Pat. Off. . |
| 0 532 035 A2 | 3/1993 | European Pat. Off. . |
| 0532035 | 3/1993 | European Pat. Off. ............ 604/385.1 |
| 0 685 212 A2 | 12/1995 | European Pat. Off. . |
| 2209672 | 9/1987 | United Kingdom ................ 604/385.2 |
| 2209672 | 5/1989 | United Kingdom . |
| 2263914 | 8/1993 | United Kingdom ................ 604/385.2 |
| 2 289 418 | 11/1995 | United Kingdom . |
| WO93/12746 | 7/1993 | WIPO . |
| WO95/27459 | 10/1995 | WIPO . |

Primary Examiner—John G. Weiss
Assistant Examiner—Bruce E. Snow
Attorney, Agent, or Firm—Patricia A. Charlier; Thomas M. Gage

[57] ABSTRACT

An absorbent article includes a moisture barrier, a bodyside liner bonded to the moisture barrier, and an absorbent structure disposed between the bodyside liner and moisture barrier. Elasticized bumpers which function as three-dimensional physical barriers to liquid movement are disposed in the margins of the article. The elasticized bumpers include an internal barrier structure and an elasticized cover disposed over the internal barrier structure and bonded to one of the margins. In particular embodiments, the elasticized cover is formed of a hydrophobic material, is unadhered to the internal barrier structure, and/or is comprised of elastic strands of variable degrees of power.

9 Claims, 7 Drawing Sheets

5,769,835

ABSORBENT ARTICLE HAVING TUBULAR, ELASTICIZED BUMPERS

BACKGROUND OF THE INVENTION

The present invention relates to articles for containing and absorbing body fluids. More particularly, the invention pertains to an absorbent article including elasticized bumpers that conform to the shape of the wearer and reduce the potential for side leakage.

Disposable absorbent articles such as diapers, training pants, feminine care products and adult incontinence products have been constructed in an effort to contain and absorb urine and other body exudates. Most of these absorbent articles include several common components. Specifically, disposable absorbent articles routinely include a liquid permeable bodyside liner, a liquid impermeable backing sheet, and an absorbent material disposed between the bodyside liner and the backing sheet. These products also include some form of attachment system, although the specific type may vary among fastening tapes, belts, garment adhesive, elastic straps, mechanical fasteners, integral side panels, or the like.

One common concern in designing the foregoing type of disposable absorbent article is leakage, and in particular leakage of liquid from the side edges of the article. A wide variety of special components have been developed and added to absorbent articles in order to reduce the instances of side leakage. For instance, many absorbent articles include elastic structures positioned along the sides of the absorbent material and stretch bonded to the bodyside liner and backing sheet. The elastic structures are intended to gather the side portions of the article and form seals, gaskets or barriers to impede the flow of liquid past the side edges of the article. In addition to leg elastic structures, absorbent articles have also included elasticized containment flaps which stand up from the surface of the bodyside liner, again in an attempt to control the movement of liquid as well as other body wastes toward the side edges of the article.

Despite the demonstrable improvement in containing body wastes, and in particular urine, afforded by such elasticized structures, absorbent articles are still subject to failures in the form of leakage past their side edges. This may be due in part to the fact that individual elastic elements have been relied upon to provide a relatively high degree of contraction of the article. Consequently, the gatherable materials to which the individual elastic elements are attached tend to form many rugosities, such as wrinkles or creases along the length of the elastic elements when they are in a semi-relaxed state. These rugosities formed in the gatherable material by the individual elastic elements may form a great number of relatively small leakage sites. Additionally, these rugosities tend to rub against the skin of the wearer during use and may contribute to irritation or chafing.

Therefore, what is lacking and needed in the art is an improved absorbent article having elasticized structures that present three-dimensional physical barriers to liquid movement, and specifically elasticized structures that reduce the instances of leakage from the side edges of the article by minimizing or eliminating the formation of rugosities which may result in leakage sites and skin irritation.

SUMMARY OF THE INVENTION

In response to the discussed deficiencies in the prior art, a new disposable absorbent article has been developed. The absorbent article includes elasticized bumpers positioned between an absorbent structure and side edges of the article. The components of the elasticized bumper are desirably selected to retard lateral movement of liquid away from the absorbent structure and minimize or eliminate the formation of rugosities which could otherwise form leakage passageways toward the side edges of the article or cause skin irritation.

In one aspect, the invention concerns an absorbent article including a moisture barrier having longitudinal end edges and longitudinal side edges extending between the end edges, a bodyside liner bonded to the moisture barrier, and an absorbent structure disposed between the bodyside liner and moisture barrier. The bodyside liner, the moisture barrier, or both form opposite margins which extend beyond the absorbent structure. An elasticized bumper of the absorbent article is disposed in each of the margins. Each elasticized bumper includes an internal barrier structure and an elasticized cover operatively joined to one of the margins. The elasticized cover encircles the internal barrier structure but is unadhered to the internal barrier structure. This aspect of the invention provides a three-dimensional physical barrier to liquid flow that resists the formation of rugosities.

Another aspect of the invention concerns an absorbent article having opposite margins and an elasticized bumper disposed in each of the margins. Each of the elasticized bumpers has a height dimension of from about 3 to about 25 millimeters, and each includes an internal barrier structure and an elasticized cover operatively joined to one of the margins. The elasticized cover encircles the internal barrier structure but is unadhered to the internal barrier structure. Either the internal barrier structures or the elasticized covers are hydrophobic.

In another aspect, the invention concerns an absorbent article having opposite margins and an elasticized bumper disposed in each of the margins. Each of the elasticized bumpers includes an internal barrier structure and an elasticized cover encircling the internal barrier structure. The elasticized cover is operatively joined to one of the margins and includes at least one casing layer and at least 4 elastic strands operatively joined to the casing layer. The elastic strands are arranged generally parallel to one another and include at least one elastic strand having greater elastic power than at least one other elastic strand.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Figure 1:
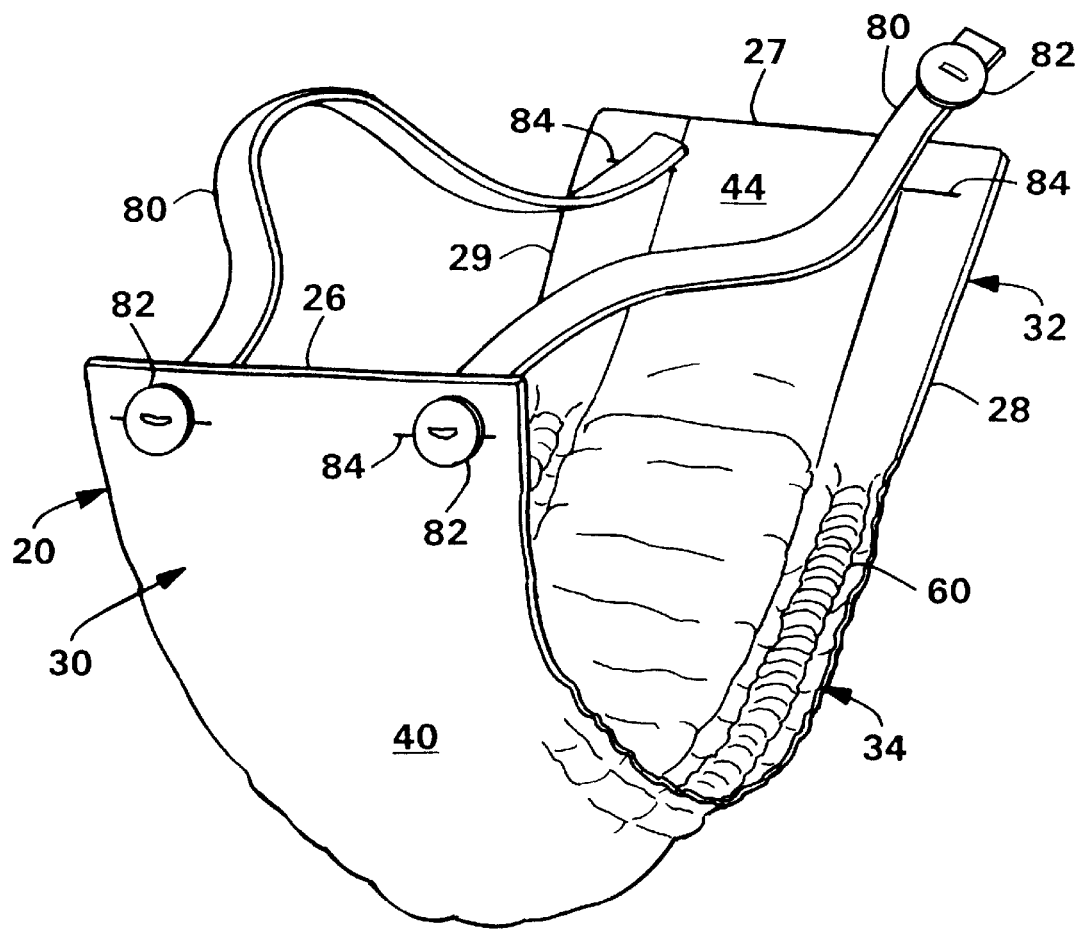
FIG. 1 representatively shows a perspective view of a disposable absorbent article according to the present invention.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use and not intended to be washed and reused.

(c) "Disposed," "disposed on," "disposed with," "disposed at," "disposed near" and variations thereof are intended to mean that one element can be integral with another element, or that one element can be a separate structure bonded to or placed with or placed near another element.

(d) "Elastic," "elasticized" and "elasticity" mean that property of a material by virtue of which it tends to recover its original size and shape after removal of a force causing a deformation.

(e) "Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 200 percent, of its relaxed length and recover, upon release of an applied force, at least 50 percent of its elongation.

(f) "Extension," "extend" and "extended" mean the change in length of a material due to stretching, expressed in units of length.

(g) "Fabrics" is used to refer to all of the woven, knitted and nonwoven fibrous webs.

(h) "Flexible" refers to materials which are compliant and which will readily conform to the general shape and contours of the wearer's body.

(i) "Force" includes a physical influence exerted by one body on another which produces acceleration of bodies that are free to move and deformation of bodies that are not free to move.

(j) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(k) "Integral" is used to refer to various portions of a single unitary element rather than separate structures bonded to or placed with or placed near one another.

(l) "Inward" and "outward" refer to positions relative to the center of an absorbent garment, and particularly transversely and/or longitudinally closer to or away from the longitudinal and transverse center of the absorbent garment.

(m) "Layer" when used in the singular can have the dual meaning of a single element or a plurality of elements.

(n) "Liquid impermeable" when used to describe a layer or laminate means that liquid such as urine will not pass through the layer or laminate under ordinary use conditions in a direction generally perpendicular to the plane of the layer or laminate at the point of liquid contact.

(o) "Member" when used in the singular can have the dual meaning of a single element or a plurality of elements.

(p) "Nonwoven web" means a web of material which is formed without the aid of a textile weaving or knitting process.

(q) "Operatively joined" and "operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(r) "Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 200 percent, of its relaxed length when it is bonded to the other member.

(s) "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

(t) "Unadhered" refers to an absence of bonds of sufficient strength to withstand the forces typically encountered during ordinary wearing of the diaper.

These terms may be defined with additional language in the remaining portion of the specification.

DETAILED DESCRIPTION OF THE PREFERRED EMBODIMENTS

Figure 2:
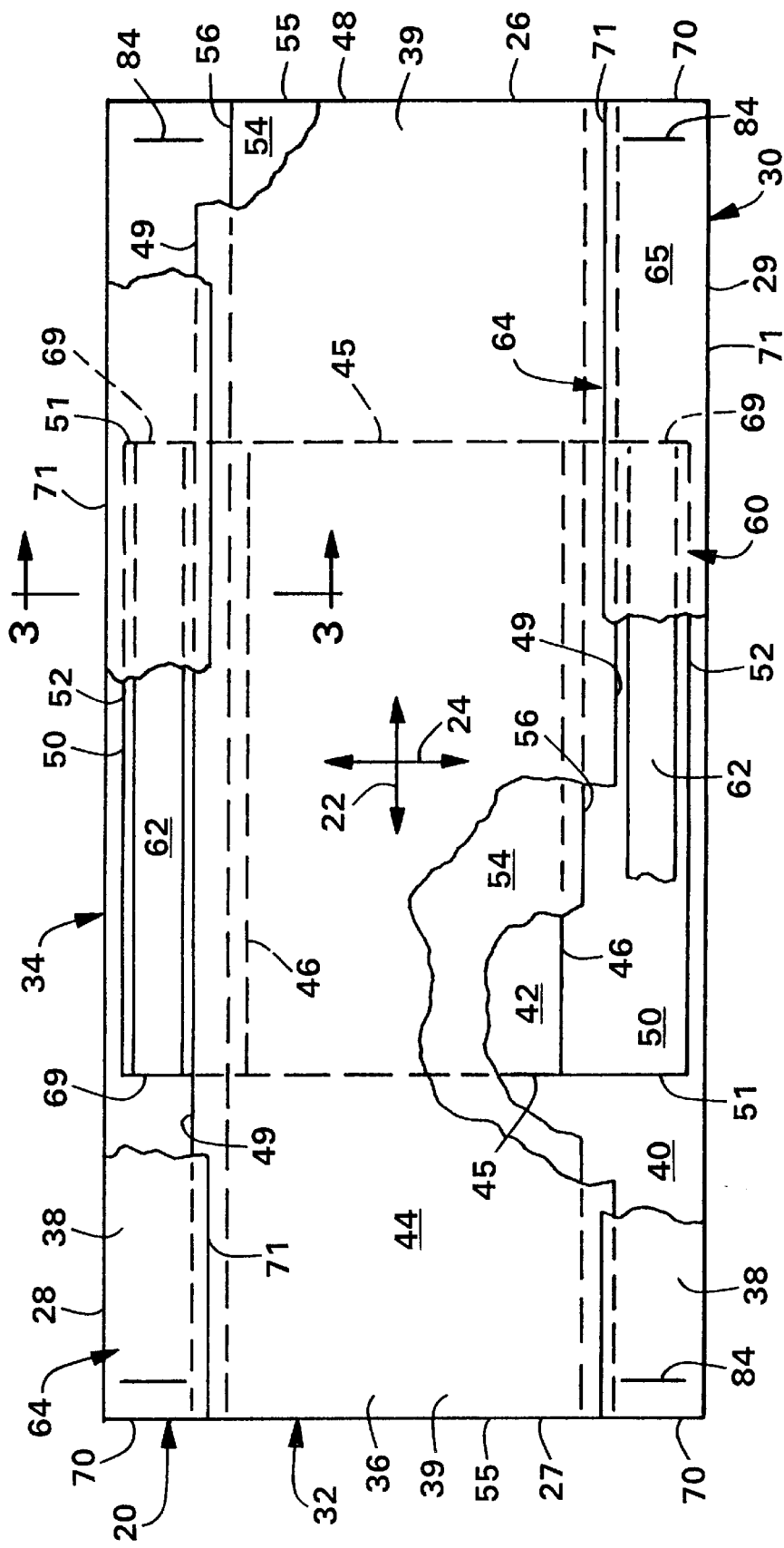
FIG. 2 representatively shows a top plan view of several components of the disposable absorbent article shown in FIG. 1, in a flat and stretched condition and with portions broken away for purposes of illustration.
Figure 3:
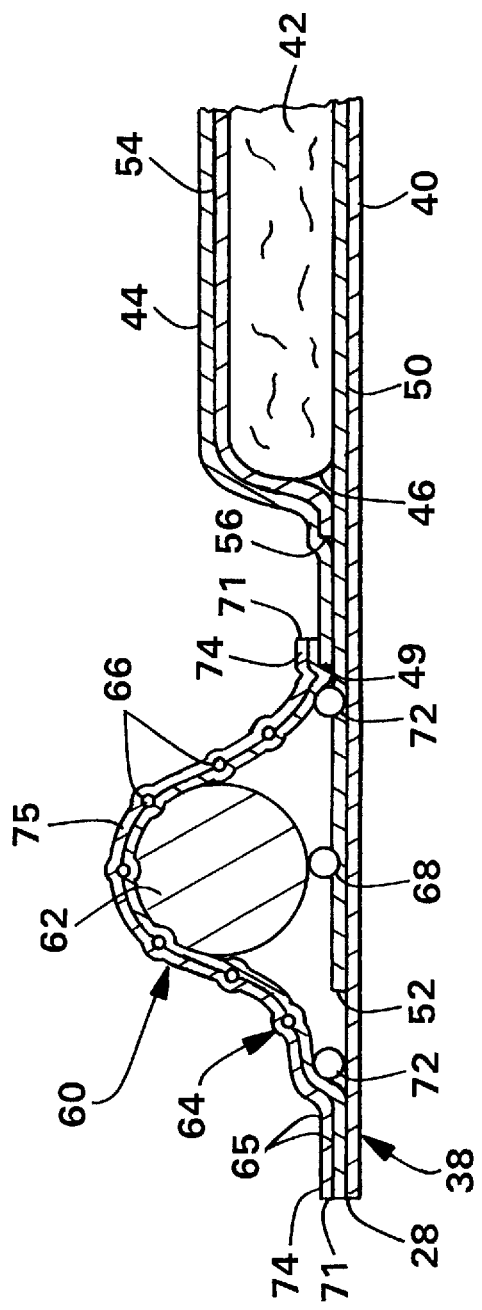
FIG. 3 representatively shows an enlarged section view taken generally from the plane of the line 3—3 in FIG. 2.

With reference to FIGS. 1–3, an absorbent article formed according to the invention is shown for purposes of illustration as a disposable undergarment 20 for adult incontinence. The invention may also be embodied in other types of garments, such as other adult incontinence articles, diapers, feminine care products, training pants, reusable absorbent articles, underwear, bathing suits, other personal care or health care garments, or the like.

In general, the undergarment 20 includes elasticized bumpers 60 disposed in each of the side margins 38 of the undergarment. In one embodiment, each elasticized bumper 60 includes an internal barrier structure 62 bonded to the side margin 38 and an elasticized cover 64 disposed over the internal barrier structure. In one aspect of the invention, the cover 64 is formed of a hydrophobic material to retard the spread of liquid toward the side edges 28 and 29 of the undergarment 20. In another aspect of the invention, the elasticized cover 64 includes lateral portions 74 that are bonded to the side margins 38, leaving the elasticized cover not directly adhered to the internal barrier structure 62. This permits the elasticized cover 64 to move relative to the internal barrier structure 62 and decreases the formation of large rugosities which would otherwise be caused by gathering of the internal barrier structure. In yet another aspect of the invention, the elasticized cover 64 includes at least one casing layer 65 and at least 4 elastic strands 66 operatively joined to the casing layer. The elastic strands 66 are arranged generally parallel to one another and within about 8 millimeters of neighboring strands to improve uniform gathering of the cover 64 and again minimize the formation of rugosities. In an alternative embodiment, an elasticized bumper 202 includes an elasticized cover 64 that fully encircles the internal barrier structure 62.

The illustrated undergarment 20 defines a longitudinal axis or center line and a transverse axis or center line, represented by arrows 22 and 24 in FIG. 2. The undergarment 20 has opposite, front and back longitudinal end edges 26 and 27, and first and second longitudinal side edges 28 and 29 that extend between the longitudinal end edges. The undergarment 20 includes a first or front waist region 30, a second or back waist region 32, and an intermediate, crotch region 34 positioned between and interconnecting the front and back waist regions. The outer edges of the undergarment 20 define a periphery 36 in which the longitudinally extending side margins are designated 38 and the laterally extending end margins are designated 39. The end edges 26 and 27 and side edges 28 and 29 are shown as generally straight, but optionally, may be curvilinear and contoured.

The front waist region 30 is contiguous with the front end edge 26 and extends longitudinally inward therefrom toward the transverse center line 24 of the undergarment 20. The back waist region 32 is contiguous with the back end edge 27 and extends longitudinally inward therefrom toward the transverse center line 24. The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer and covers the lower torso of the wearer. Thus, the crotch region 34 is the area where insults of urine typically occur in the undergarment or other disposable absorbent article.

The undergarment 20 includes a substantially liquid impermeable moisture barrier 40, an absorbent structure 42 (FIGS. 2 and 3) disposed on the moisture barrier, and a substantially liquid permeable bodyside liner 44 bonded to the moisture barrier to sandwich the absorbent structure therebetween. The moisture barrier 40 and bodyside liner 44 are desirably longer and wider than the absorbent structure 42 so that the peripheries of the moisture barrier and bodyside liner may be bonded together using ultrasonic bonds, thermal bonds, adhesives, or other suitable means. The periphery of the moisture barrier 40, the bodyside liner 44, or the peripheries of both, typically form the side and end margins 38 and 39 of the undergarment 20. The absorbent structure 42 may also be bonded to the moisture barrier 40 and/or the bodyside liner 44 using ultrasonic bonds, thermal bonds, adhesives, or other suitable means.

The moisture barrier 40 desirably comprises a material that is formed or treated to be liquid impermeable. Alternatively, the moisture barrier 40 may comprise a liquid permeable material and other suitable means (not shown), such as a liquid impermeable layer associated with the absorbent structure 42, may be provided to impede liquid movement away from the absorbent structure. The moisture barrier 40 may also be gas permeable, such that gases encountered during use of the absorbent article are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, wovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene and polyethylene medium-crimped bicomponent fibers in a 50/50 side-by-side configuration.

The absorbent structure 42 comprises materials adapted to absorb and retain liquid waste. The absorbent structure 42 may comprise various absorbent materials, such as an airformed batt of cellulosic fibers such as wood pulp fluff or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent structure 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent structure 42 may also include tissue layers or acquisition or distribution layers to help maintain the integrity of fibrous absorbents or transport liquids (not shown).

In the illustrated embodiment, the moisture barrier 40 extends the full length and width of the undergarment 20 and thus defines in part the front and back end edges 26 and 27 and the first and second side edges 28 and 29. As best shown in FIG. 2, the absorbent structure 42 has opposite end edges 45 and opposite side edges 46 that extend between the end edges. The end and side edges 45 and 46 of the absorbent structure 42 are desirably spaced inward from the end edges 26 and 27 and side edges 28 and 29 of the undergarment 20. In the longitudinal direction, for example, the absorbent structure 42 desirably has a length of from about 50 to about 95 percent of the undergarment 20. The bodyside liner 44 also includes opposite end edges 48 and opposite side edges 49 that extend between the end edges. In the illustrated embodiment, the end edges 48 extend to the full length of the undergarment 20, although the side edges 49 are spaced inward from the side edges 28 and 29 of the undergarment. Alternatively, of course, the side edges 49 of the bodyside liner 44 could extend to or independently form the side edges 28 and 29 of the undergarment 20.

As best shown in FIG. 3, the undergarment 20 desirably includes a carrier sheet 50 disposed between the absorbent structure 42 and the moisture barrier 40. The carrier sheet 50 may serve as a carrier web for the absorbent structure 42 during high speed manufacturing processes to manufacture the undergarment 20. The carrier sheet 50 desirably comprises a hydrophilic, air and liquid permeable material such as a high wet strength tissue. For example, the carrier sheet 50 may comprise a 17 grams per square meter (gsm) web of cellulose fibers. Alternatively, the carrier sheet 50 may comprise nonwettable nonwoven webs formed of polyolefins, polyesters, rayon or the like, desirably with relatively low basis weights, such as less than about 30 gsm, and with sufficient mechanical strength to withstand handling in a high-speed manufacturing process, a film, or the like. The carrier sheet 50 has opposite end edges 51 and opposite side edges 52 that extend between the end edges. The end edges 51 of the carrier sheet 50 may be coextensive with the end edges 45 of the absorbent structure 42. The width of the carrier sheet 50 is desirably such that the side edges 52 extend transversely outward of the absorbent structure 42 into the side margins 38 of the undergarment 20.

The illustrated undergarment 20 also includes a liquid handling layer 54 that is disposed between the bodyside liner 44 and the absorbent structure 42. The liquid handling layer 54 has opposite end edges 55 and opposite side edges 56 that extend between the end edges. Desirably, but not necessarily, the length of the liquid handling layer 54 is such that the end edges 55 are coextensive with the end edges 26 and 27 of the undergarment 20. Thus, the liquid handling layer 54 is positioned in the front and back waist sections 30 and 32 between the absorbent structure 42 and the end edges 26 and 27 of the undergarment 20. The width of the liquid handling layer 54 is suitably such that the side edges 56 are positioned between the side edges 46 of the absorbent structure 42 and the side edges 28 and 29 of the undergarment 20.

The liquid handling layer 54 is desirably present in the front and back waist sections 30 and 32 to draw liquid that may be present in those regions away from the interior surface of the undergarment 20 and thus away from the skin of a wearer. The liquid handling layer 54 may comprise an absorbent material such as one or more cellulose tissue sheets or an airlaid web of hydrophilic fibers. Alternatively, the liquid handling layer 54 may comprise a material adapted to rapidly take in and/or distribute liquids. Any woven or nonwoven web adapted to quickly take in and/or transport liquids may be suitable for the liquid handling layer 54. For example, the liquid handling layer 54 may comprise a nonwoven web such as a spunbonded, meltblown or bonded-carded web composed of synthetic polymer filaments or fibers such as polypropylene, polyethylene, polyesters or the like or a web of natural polymer filaments or fibers as rayon or cotton. The liquid handling layer 54 desirably comprises a material that is formed or treated to be substantially hydrophilic. Examples of suitable materials are also described in U.S. Pat. No. 5,192,606 issued Mar. 9, 1993, to D. Proxmire et al.; U.S. Pat. No. 4,798,603 issued Jan. 17, 1989, to S. Meyer et al.; U.S. Pat. No. 5,364,382 issued Nov. 15, 1994, to M. Latimer et al.; U.S. patent application Ser. No. 757,760 of W. Hanson et al. filed Sep. 11, 1991 (Attorney docket No. 9922); U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, and filed Mar. 4, 1994 (Attorney docket No. 11,256); and U.S. patent application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, and filed Mar. 4, 1994 (Attorney docket No. 11,387); the disclosures of which are hereby incorporated by reference.

In the illustrated embodiment, the carrier sheet 50 is disposed between the moisture barrier 40 and the absorbent structure 42. Alternatively, the carrier sheet 50 may be disposed between the absorbent structure 42 and the bodyside liner 44. In such case, the carrier sheet 50 should be liquid permeable and may function as the liquid handling layer 54. Further, the liquid handling layer 54 may be disposed between the absorbent structure 42 and the moisture barrier 40.

The bodyside liner 44 is formed of a liquid permeable material so that liquid waste, and possibly semi-solid waste as well, can pass through the liner and be absorbed by the absorbent structure 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably non-elastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Union Carbide Chemicals and Plastics Company, Inc., of Danbury, Conn., U.S.A. under the trade designation Triton X-102.

The undergarment 20, portions of which are in a stretched and laid flat condition in FIG. 2, is illustrated as having a rectangular periphery 36. Of course, the undergarment 20 may optionally be hourglass-shaped, I-shaped, T-shaped, or irregularly-shaped. The general shape of the absorbent structure 42 may correspond to the shape of the undergarment 20 or assume a different shape.

To conform the side margins 38 of the undergarment 20 to the body of the wearer and minimize the likelihood of leakage from the side edges 28 and 29, the undergarment is provided with an elasticized bumper 60 in each side margin 38. The elasticized bumpers 60 are disposed on the moisture barrier 40 at least in the crotch region 34, but they may also extend into the front and back waist regions 30 and 32. The elasticized bumpers 60 may be generally straight or curved and may but need not follow the peripheral shape of either the side edges 46 of the absorbent structure 42 or the side edges 28 and 29 of the undergarment 20. In one alternative embodiment, the elasticized bumpers 60 may be positioned in one or both of the waist regions 30 and 32, such as in end margins 39, oriented parallel to the transverse axis 24 instead of or in addition to being positioned along the side edges 28 and 29 (not shown).

In the embodiment shown in FIGS. 1–3, the elasticized bumpers 60 comprise an internal barrier structure 62 disposed on the moisture barrier 40 and a cover 64 disposed over the internal barrier structure. The illustrated cover 64 includes a pair of casing layers 65 and a plurality of strands 66 of elastic positioned between and operatively joined to the casing layers (FIG. 3). Alternatively, the cover 64 may comprise a single elastomeric fabric or a composite of a single casing layer and one or more elastomeric elements or layers (not shown).

The internal barrier structures 62 of the undergarment 20 shown in FIGS. 1–3 are oriented parallel to the longitudinal axis 22 and positioned between the side edges 46 of the absorbent structure 42 and the side edges 28 and 29 of the undergarment. In particular, the internal barrier structures 62 are suitably spaced from the side edges 46 of the absorbent structure 42 by from 0 to about 7 centimeters (cm), and particularly from about 0.5 to about 3 cm. Also, the internal barrier structures 62 are suitably positioned from about 0.5 to about 4 cm from the side edges 28 and 29, such as from about 1 to about 3 cm from the side edges. The length of the internal barrier structures 62 is suitably comparable to the length of the crotch region 34 but may be up to the full length of the undergarment 20. For convenience of manufacturing though, as discussed in greater detail below, the length of the internal barrier structures 62 is desirably the same as the length of the absorbent structure 42.

In the illustrated embodiment, the internal barrier structures 62 are positioned transversely inward from the side edges 52 of the carrier sheet 50. A bead 68 of adhesive or other suitable means is used to bond the internal barrier structures 62 to the carrier sheet 50 (FIG. 3). The adhesive bead 68 may also be effective to penetrate through the carrier sheet 50 and bond the carrier sheet to the moisture barrier 40. Desirably, the adhesive bead 68 is continuous along the length of the internal barrier structure 62 and does not allow liquid to penetrate between the internal barrier structure and the moisture barrier 40.

The internal barrier structures 62 desirably function to elevate the elasticized bumpers 60 from the plane of the undergarment 20 defined by the longitudinal and transverse axes 22 and 24. In particular, the elasticized bumpers 60 suitably have a height dimension measured from the plane of the moisture barrier 40 of from about 3 to about 25 millimeters (mm), and particularly from about 5 to about 15 mm. The width of the elasticized bumpers 60 is desirably from about 2 to about 30 mm, and more particularly, from about 5 to about 15 mm, for improved performance.

The internal barrier structures 62 may be formed of any material which allows the elasticized bumpers 62 to conform to the shape of the wearer. In one particular embodiment, the internal barrier structures 62 comprise a resilient sliver structure formed of 100 percent 2.2 denier hydrophobic polypropylene staple fibers having a length of 3.8 cm and available from Hercules Inc. of Wilmington, Del., U.S.A., under the trade designation T190. The term "sliver" refers generally to a continuous untwisted strand or bundle of flat fibers produced by a conventional carding process. Carding separates fibers from each other, lays them parallel, forms them into a thin web, and then condenses them into the sliver. The process for forming the sliver structure is disclosed in U.S. Pat. No. 5,133,371 issued Jul. 28, 1992, to Sivess, which is incorporated herein by reference.

The sliver structure may be composed of a wide variety of cardable fibers, but is desirably comprised of those fibers which are substantially nonabsorbent, nonelastomeric and hydrophobic in nature. The internal barrier structures 62 may also be hydrophilic, particularly in instances where the cover 64 is formed or treated to be hydrophobic. The internal barrier structures 62 may comprise additional components to enhance the resiliency of the structures, such as foams or resilient fibers. Ends 69 of the side barrier structures 62 are desirably but not necessarily coextensive with the ends 51 of carrier sheet 50 and the ends 45 of the absorbent structure 42.

The cover 64 is formed of an elastomeric material or composite adapted to gather the side margins 38 of the undergarment 20 and maintain the elasticized bumpers 60 against the skin of the wearer. The cover 64 includes opposite longitudinal ends 70 and opposite longitudinal sides 71 extending between the ends. The ends 70 of the cover 64 in the illustrated embodiment are coextensive with the end edges 26 and 27 of the undergarment 20, and one side edge 71 of each cover 64 is desirably coextensive with or adjacent to a side edge 28 or 29 of the undergarment.

With particular reference to FIG. 3, the covers 64 also include opposite lateral portions 74 with a central portion 75 positioned between and interconnecting the lateral portions. The lateral portions 74 are contiguous with the side edges 71 of the covers 64. The covers 64 are disposed on the internal barrier structures 62 and have sufficient width such that the lateral portions 74 can be bonded to the moisture barrier 40 with beads 72 of adhesive or other suitable means. As illustrated, the adhesive beads 72 nearest the side edges 28 and 29 directly bond the covers 64 to the moisture barrier 40, while the adhesive beads 72 nearest the absorbent structure 42 directly bond the covers 64 to the carrier sheet 50 and are desirably effective to penetrate through the carrier sheet and bond the carrier sheet to the moisture barrier. Both adhesive beads 72 are desirably continuous along the length of the covers 64 and do not allow liquid to penetrate between the covers and the moisture barrier 40. Notably, the central portions 75 of the covers 64 are desirably not bonded directly to the internal barrier structures 62. Rather, the inner surfaces of the covers 64 are free to slide over the exterior surfaces of the internal barrier structure 62 to minimize the formation of rugosities.

The casing layers 65 desirably define the end and side edges 70 and 71 of the cover 64. The casing layers 65 may be formed of any flexible, gatherable material. In particular embodiments, the casing layers 65 are either impermeable to liquids or formed or treated to be hydrophobic. Less desirably, the casing layers 65 may be hydrophilic or liquid permeable and the internal barrier structures 62 are formed of a hydrophobic material. One particular material that may be useful in forming the casing layer 65 is a thermally point bonded web of bicomponent spunbond fibers having a basis weight of from about 10 to about 27 gsm (0.3–0.8 osy), such as from about 12 to about 20 gsm (0.4–0.6). The fibers are 50/50 side-by-side polypropylene/polyethylene bicomponent fibers constructed of polyethylene available from Dow Chemical Company of Midland, Mich., U.S.A., under the trade designation ASPUN™ 6811A and polypropylene available from Exxon Chemical Company of Houston, Tex., U.S.A., under the trade designation PP3445. The extruded fibers suitably have an average fiber diameter of between about 17 and 25 microns, such as about 23 microns, and a low crimp, such as approximately one or fewer crimps per extended inch using ASTM test method D-3937-82. The web may be produced according to the processes for production of bicomponent webs as described in U.S. Pat. No. 5,382,400 issued Jan. 17, 1995, to Pike et al., the disclosure of which is incorporated herein by reference. Other suitable materials for use as the casing layer 65 include copolymer, polypropylene, polyester or nylon spunbonds, combinations of these polymers in bicomponent constructions or in blends, and carded webs composed of suitable cardable fibers. The fibers may have varying degrees of crimp; however, the crimp is desirably less than approximately 15 or fewer crimps per extended inch. Also, the webs may be bonded by other suitable means such as through air bonding.

The cover 64 may alternatively comprise only a single casing layer 65 with the elastic strands 66 bonded to the single casing layer on the surface facing the internal barrier structure 62. Still alternatively, the cover 64 may be composed of a substantially elastomeric layer, such as polymer films, woven fabrics, nonwoven fabrics or the like, as well as combinations thereof, rather than a plurality of strands of elastomeric material. For example, the cover 64 can be composed of a stretch-bonded-laminate (SBL) material, a neck-bonded-laminate (NBL) material, an elastomeric film, an elastomeric foam material, or the like. For example, suitable meltblown elastomeric fibrous webs for forming the cover 64 are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Morman; U.S. Pat. No. 5,336,545 issued Aug. 9, 1994 to Morman; and U.S. patent application Ser. No. 08/276,924 by Haffner et al., filed Jul. 19, 1994, and titled "COMPOSITE ELASTIC NECK-BONDED MATERIAL" (Attorney Docket No. 8704.4); the disclosures of which are hereby incorporated by reference.

In the illustrated embodiment, elastic strands 66 are disposed between the casing layers 65 and operatively joined thereto using adhesives or other suitable means (FIG. 3). For example, the elastic strands 66 may be adhesively bonded to the casing layers 65 using a 5 gsm application of a hot melt, rubber-based adhesive available from Findley Adhesives of Wauwatosa, Wis., U.S.A., under the trade designation H-2096. The elastomeric component of the adhesive is available from the Shell Chemical Company of Houston, Tex., U.S.A., under the trade designation KRATON. The elastic strands 66 may be formed of a dry-spun coalesced multi-filament elastomeric thread sold under the trade name LYCRA® and available from E. I. Du Pont de Nemours and Company. Alternatively, the elastic component of the cover 64 may comprise other typical elastics utilized in the undergarment-making art, such as a thin ribbon of natural or synthetic rubber, a stretch bonded laminate material, other strand structures such as isoprene strands available from JPS Elastomerics, Stuart, Va., U.S.A., elastomeric films such as EVA or urethane films, hot melt elastomeric adhesives, or the like.

The number, spacing, positioning, power and overall tension of the elastic strands 66 are desirably controlled to maintain the elasticized bumpers 60 against the body of the wearer and create a physical barrier to lateral liquid flow, while at the same time minimizing the formation of rugosities which could create leakage sites. In particular embodiments, the covers 64 comprise at least 4 elastic strands 66, and particularly from 4 to 12 elastic strands, and more particularly from 6 to 8 elastic strands. The elastic strands 66 are spaced from neighboring strands by less than about 8 mm, and particularly by from about 3 to about 6 mm from neighboring strands for improved performance. The elastic strands 66 are suitably spaced from the adhesive beads 72 so the elastic characteristics of the strands are not defeated. The individual elastic strands 66 may be identical to one another. Alternatively, however, at least one of the elastic strands 66 has greater elastic power than at least one of the other elastic strands 66. Further, the elastic strands 66 having greater elastic power are desirably located on top of the interior barrier structures 62, which corresponds to the central portion 75 of the cover 64. In the illustrated embodiment (FIG. 3), for example, the cover 64 includes 7 elastic strands 66, and 3 of those strands desirably have greater elastic power than the remaining 4 strands. The 3 strands of greater elastic power are desirably centrally located between the adhesive beads 72 that bond the cover 64 to the side margins 38. This configuration has the benefit of positioning the elastic strands 66 with greater elastic power closer to the body of the wearer. As a result, the undergarment 200 tends to more easily assume a "U" shape as viewed in the longitudinal direction 22. The "U" shape is best suited to conform to the body of the wearer and aid in formation of a leakage barrier.

The term elastic power is used herein to mean the retraction force of one elastic member compared to the retraction force of another elastic member. One elastic member may have more elastic power than another member due to the nature of the materials of which they are made, the levels of elongation of the elastic members, the decitex of elastic members, or the like. By way of illustration, a cover 64 may incorporate one set of elastic strands 66 having a decitex of 620 and another set of elastic strands having a decitex of 940. Both sets of strands may be stretched to 270 percent elongation and bonded to the casing layer 65. The set of 940 decitex strands could be positioned in the central portion 75 of the cover 64 and the set of 620 decitex strands could be positioned in the lateral portions 74 of the cover.

The elasticized bumpers 60 of the present invention desirably provide relatively high degrees of tension without creating localized regions of high tension that contribute to skin irritation. In particular, the side margins 38 of the undergarment 20 desirably possess a side margin tension of from about 0.06 to about 0.30 kilograms. One suitable procedure for determining the side margin tension of an absorbent article is the Product Tension Test set forth in the Test Methods section below.

The attachment system in the illustrated embodiment includes a pair of strap members 80 and fastening components to releasably attach the strap members to the front and back waist regions 30 and 32 (FIG. 1). The fastening components include a retainer 82 in the form of a button bonded at each end of each strap member 80. The retainers 82 may be releasably secured in slits 84 formed near the corners of the undergarment 20 in the moisture barrier 40 and other components. When the undergarment 20 is positioned on the wearer, the straps 80 extend between the front and back slits 84 so that the retainers 82 may be releasably secured in the slits. Optionally, other types of attachment systems, such as tapes, stretchable side panels, self-engaging geometric shaped materials, such as hooks, loops, bulbs, mushrooms, arrowheads, balls on stems, or the like, may be employed. The illustrated attachment system as well as alternatives thereto are described in U.S. Pat. No. 4,315,508 issued Feb. 16, 1982, to Bolick and U.S. Pat. No. 5,386,595 issued Feb. 7, 1995, to Kuen et al., the disclosures of which are incorporated herein by reference.

The strap members 80 (FIG. 1) are each generally rectangular strips of material, which material is desirably an elastic material capable of stretching to approximately 2.8 to 3 times its relaxed length. The strap members 80 desirably have a length from about 15 to about 41 centimeters (cm.), and a width from about 1 to about 5 cm. For example, each strap member 80 may be 28 cm. long and 2.5 cm. wide. The cut ends of the strap members 80 may be bonded by ultrasonics, adhesives or other suitable means to prevent raveling.

In use, the undergarment 20 is positioned on the wearer and secured with the attachment system. The function of the elasticized bumpers 60 includes both gathering the undergarment 20 in the longitudinal direction 22 to conform the garment to the body as well as presenting a raised physical barrier to impede the lateral movement of liquids. In this regard, the elasticized bumpers 60 and in particular the covers 64 are formed of materials that resist liquid movement in the transverse direction. In particular embodiments, the covers 64 are desirably unadhered to the underlying internal barrier structures 62 to minimize the formation of large rugosities along the length of the elasticized bumpers. Also in particular embodiments, the elasticized bumpers 60 are constructed of individual elastic strands 66 and the number and spacing of the strands is selected so as to minimize the formation of small rugosities along the surface of the elasticized bumpers. Both large and small rugosities would otherwise create sites where liquid could escape past an elasticized physical barrier.

Figure 4:
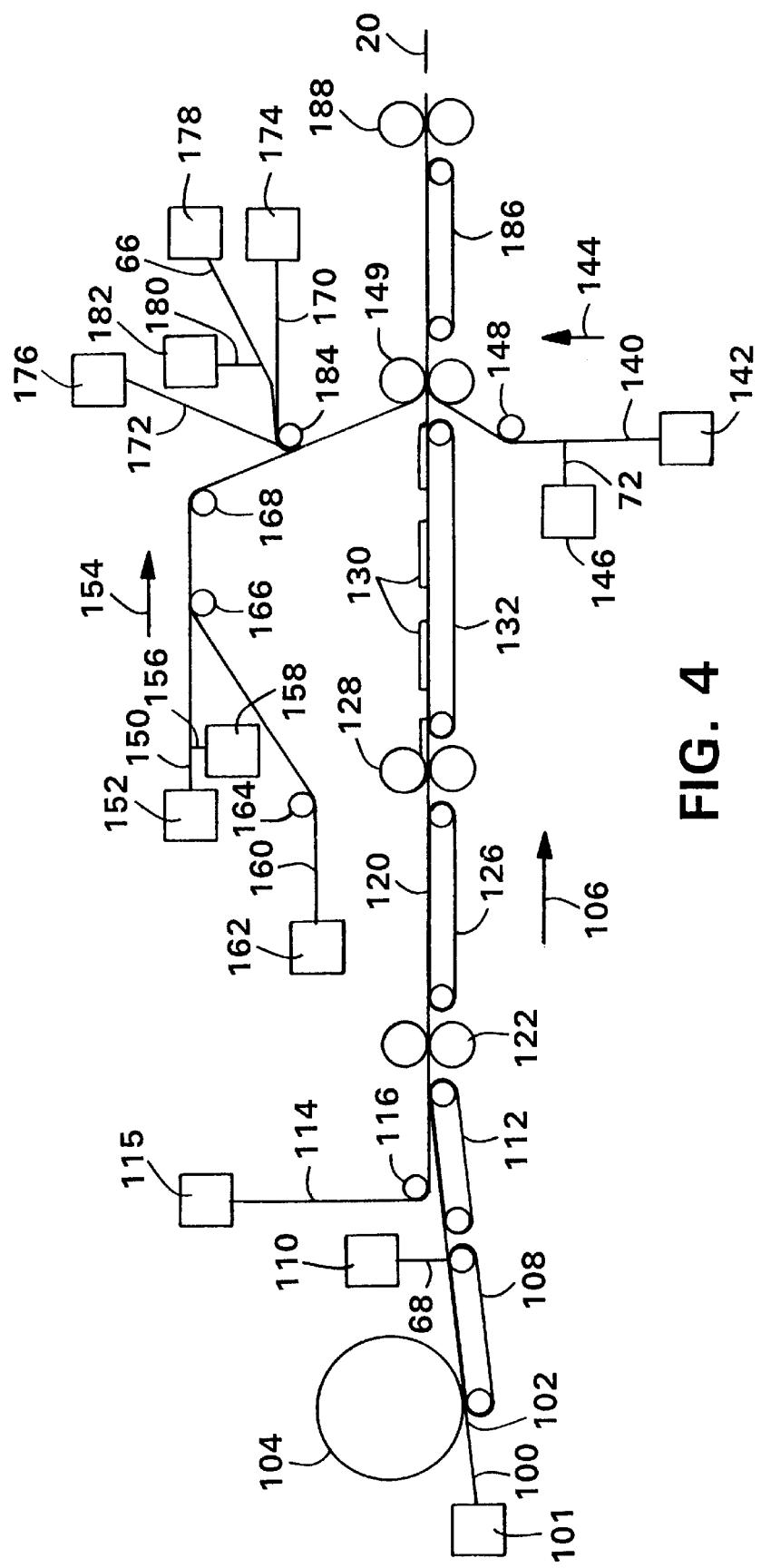
FIG. 4 representatively shows a schematic view illustrating a method of making a disposable absorbent article such as that shown in FIGS. 1–3.

A particularly efficient method for constructing the undergarment 20 described in relation to FIGS. 1–3 is schematically illustrated in FIG. 4. The method includes a number of continuous processes and does not involve any cut-and-place operations. In particular, the method includes providing a continuous carrier tissue web 100 from a forming or unwind source 101, and providing a continuous absorbent web 102 from an absorbent web source. For example, the absorbent web 102 may be supplied from a forming drum 104, as is well known in the art. The absorbent web 102 is disposed on the carrier web 100 and both are advanced in the direction of arrow 106 via transport means 108, such as a belted conveyor system or other suitable means. The absorbent web 102 is desirably narrower than the carrier web 100 and centered between the side edges 52 (FIGS. 2 and 3) of the carrier web.

The carrier and absorbent webs 100 and 102 are routed past adhesive station 110 where beads 68 of adhesive are applied to the carrier web outward of the side edges 46 (FIGS. 2 and 3) of the absorbent web. The carrier and absorbent webs 100 and 102 continue to be advanced in the direction of arrow 106 via transport means 112. A pair of continuous strands 114 of material for forming the internal barrier structures 62 of the undergarment 20 are provided from a forming or unwind source 115. The strands 114 of internal barrier material are routed past roller 116 and united with the carrier web 100 at the location of the adhesive bead 68 such that the strands 114 are bonded to the carrier web outward of the side edges 46 of the absorbent web 102.

The continuous carrier web 100, the continuous absorbent web 102, and the continuous strands 114 of internal barrier material together form a continuous in-process composite structure 120, which is transported to an optional de-bulking unit 122 which functions to shape the absorbent web 102. It will be apparent that the continuous strands 114 of internal barrier material may be bonded to the continuous carrier web 100 either prior to or after the de-bulking unit 122.

The composite structure 120 is then conveyed by transport means 126 to a web cutting mechanism 128, shown for purposes of illustration as a rotating shear. The cutting mechanism 128 transversely cuts the continuous composite structure 120 into individual, in-process composite structures 130. Each composite structure 130 comprises a carrier sheet 50, an absorbent structure 42, and a pair of internal barrier structures 62 (FIGS. 2 and 3). The carrier sheet 50 has opposite end edges 51 and opposite side edges 52. The absorbent structure 42 has opposite end edges 45 coterminous with end edges 51 of the carrier sheet 50 and opposite side edges 46 spaced inward from the side edges 52 of the carrier sheet. The internal barrier structures 62 are positioned between the side edges 46 of the absorbent structure 42 and the side edges 52 of the carrier sheet 50 and have opposite ends 69 coterminous with the end edges 51 of the carrier sheet. The individual composite structures 130 exit the cutting mechanism 128 onto transport means 132 which is travelling at a speed greater than that of transport means 126. As a result, the individual composite structures 130 become spaced from one another.

A continuous web 140 of moisture barrier material is provided from a forming or unwind source 142 and transported in the direction of arrow 144. Adhesive beads 72 are provided from an adhesive source 146 and disposed on the continuous moisture barrier web 140. Traditional leg elastics may also be bonded to the moisture barrier web 140 if desired (not shown). The moisture barrier web 140 is routed past roll 148 to an assembly station 149.

Simultaneously, a continuous web 150 of bodyside liner material is provided from a forming or unwind source 152 and transported in the direction of arrow 154. Adhesive 156 may optionally be applied to the continuous bodyside liner web 150 from an adhesive source 158. A continuous web 160 of a liquid handling material is provided from a forming or unwind source 162, routed over transport roll 164 and united with the continuous bodyside liner web 150 at another transport roll 166. The combined bodyside liner web 150 and liquid handling web 160 continue to be transported in the direction of arrow 154 past transport roll 168.

Two covers 64 are constructed and disposed over the internal barrier structures 62, although the method and apparatus for forming only one of the covers appears in FIG. 4. Each cover 64 may be constructed from a pair of continuous casing webs 170 and 172 provided from forming or unwind sources 174 and 176. Elastic strands 66 are provided from an elastic forming or unwind source 178 and operatively joined to the casing webs 170 and 172 with adhesive 180 from an adhesive source 182. The adhesive 180 may be applied over the elongated elastic strands 66 just prior to the strands coming into contact with one of the casing webs 170, as disclosed in U.S. Pat. No. 4,842,666 issued Jun. 27, 1989, to Werenicz. The adhesive 180 is desirably applied intermittently and timed to bond the elastic strands 66 to the casing webs 170 and 172 at locations corresponding to the position of the internal barrier structures 62. Alternatively, the adhesive 180 may be applied continuously to the cover 64, or applied continuously and diverted over a portion of the length of the cover using a diverting mechanism such as the air diverting system disclosed in U.S. Pat. No. 4,711,683 issued Dec. 8, 1987, to Merkatoris.

The casing webs 170 and 172 with the elastic strands 66 bonded thereto are then routed past a transport roll 184 and united with the bodyside liner web 150 and the liquid handling web 160, and all of these components are transported to the assembly station 149. It will be apparent that the components can be arranged so that the covers 64 are at least partially on top of the bodyside liner web 50 as illustrated, or alternatively positioned beneath the bodyside liner web (not shown).

The components of the undergarment 20 are united and bonded together at the assembly station 149. The individual composite structures 130 are introduced between the moisture barrier web 140 and the bodyside liner web 150. The position of the covers 64 is controlled to coincide with the position of the internal barrier structures 62. The elastic strands 66 may be disposed directly over the internal barrier structures 62. Alternatively, however, the position of the covers 64 and/or the elastic strands 66 may be controlled to concentrate the elastic strands either transversely inward or transversely outward of the internal barrier structures 62. The adhesive beads 72 function to bond the covers 64 to the moisture barrier, and other construction adhesives (not shown) may be used to bond other components together.

From the assembly station 149, the components are carried by a transport means 186 to a cutting mechanism 188 which transversely cuts the continuous components to form individual undergarments 20. The cutting mechanism 188, for example a rotary shear, is timed to cut between the individual composite structures 130 and thus sever the moisture barrier web 140, the bodyside liner web 150, the liquid handling web 160, the casing webs 170 and 172, and the elastic strands 66. Desirably, the cutting mechanism 188 severs the covers 64 at locations where the adhesive 180 has been interrupted or diverted and does not bond the elastic strands 66 to the casing layers 65. As a result, the portions of the elastic strands 66 adjacent the ends 26 and 27 of the undergarment 20 are free to snap back to the location of the adhesive 180, such as over the internal barrier structures 62. The longitudinal position of the adhesive 180 and thus the longitudinal position of the elastic strands 66 can thereby be controlled independently of the longitudinal position of the internal barrier structures 62. In a particularly desirably embodiment, the elastic strands 66 are attached to the casing layers 65 so that the effective ends of the strands are located from about 1 to about 5 cm longitudinally outward of each end 69 of the side barrier structures 62. Alternatively, the elastic strands 66 may be attached to the casing layers 65 over the full length of the undergarment 20.

The method shown in FIG. 4 of making an undergarment is particularly desirable because all of the component webs are continuously supplied to the assembly process. Advantageously, this eliminates the need to separately cut, place and register an individual component of the elasticized bumpers 60. Additionally, the length of the internal barrier structures 62 is mechanically associated with the length of the absorbent structure 42. Also, the ends 69 of the internal barrier structures 62 are conveniently contained beneath the elasticized covers 64. Further, the method allows the longitudinal and transverse position of the elastic strands 66 to be controlled independently of the position of the internal barrier structures 62.

Figure 5:
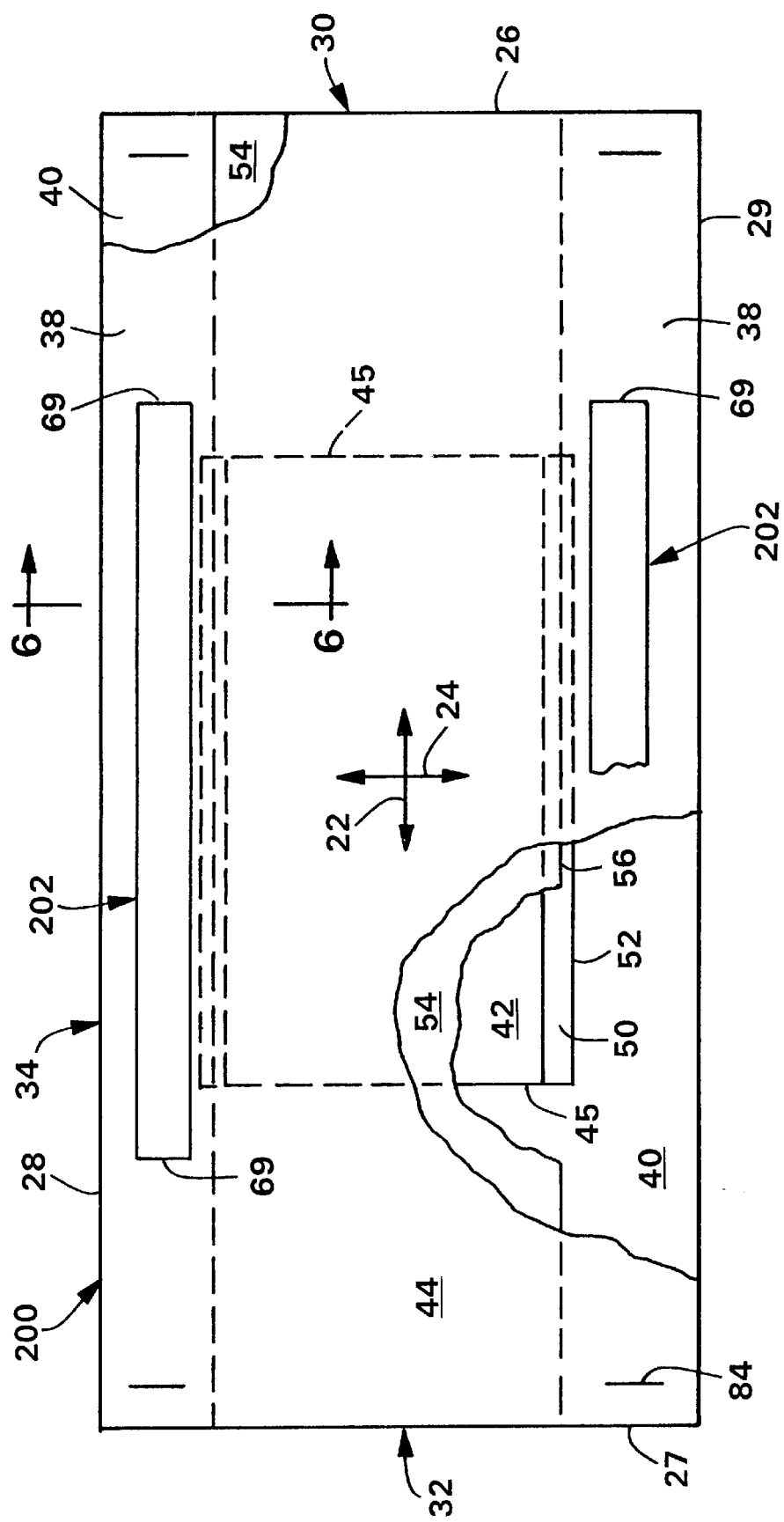
FIG. 5 representatively shows a top plan view of several components of an alternative absorbent article according to the present invention.
Figure 6:
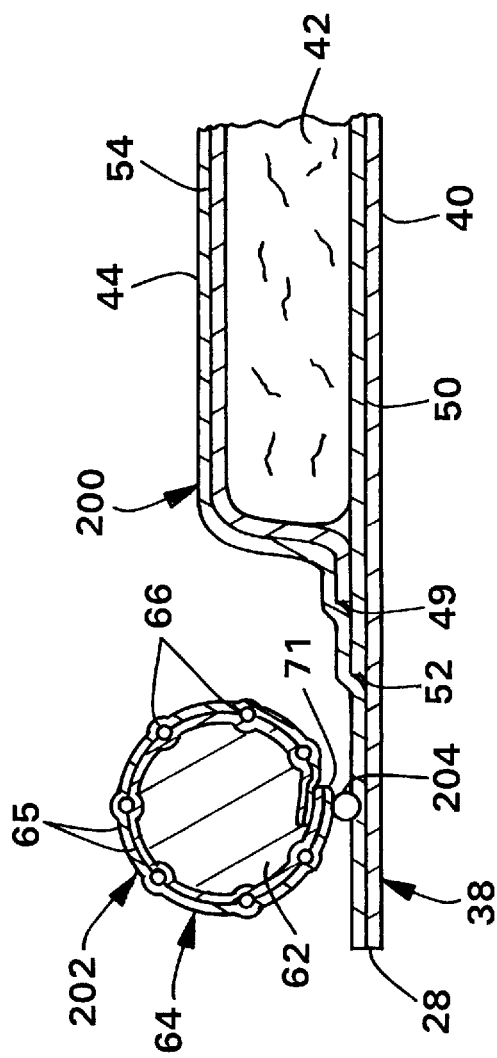
FIG. 6 representatively shows an enlarged section view taken generally from the plane of the line 6—6 in FIG. 5.

An alternative embodiment of the invention is illustrated by an undergarment 200 shown in FIGS. 5 and 6. Components similar to those previously described have been given the same reference numeral. The undergarment 200 includes an elasticized bumper 202 disposed on each side margin 38 of the undergarment. The elasticized bumpers 202 desirably extend in the longitudinal direction 22 at least as far as the ends 45 of the absorbent structures 42, and may extend beyond the ends 45 up to and including to the end edges 26 and 27 of the undergarment 200.

Each elasticized bumper 202 includes an internal barrier structure 62 and an elasticized cover 64. The cover 64 fully encircles the internal barrier structure 62 in the transverse direction 24, as illustrated in FIG. 6. The side edges 71 of the cover 64 overlap one another and are bonded together using adhesives, ultrasonic bonds, thermal bonds, mechanical bonds or other suitable means. The longitudinal ends 70 of the cover 64 may be coextensive with the ends 69 of the internal barrier structure 62, and the ends 70 and 69 may be crimped and bonded together by adhesives or other suitable means.

Each cover 64 is operatively joined to one of the side margins 38 by a bead 204 of adhesive. The adhesive bead 204 desirably is of sufficient size to penetrate through the bodyside liner 44 and is continuous along the length of the elasticized bumper 202 so that liquid cannot penetrate between the bumper and the moisture barrier 40. The covers 64 may alternatively be bonded to the side margins 38 by ultrasonic bonds, thermal bonds, mechanical bonds or other suitable means.

The illustrated cover 64 includes a pair of casing layers 65 and a plurality of elastic strands 66 positioned between and operatively joined to the casing layers. In one particular embodiment, the cover 64 includes at least 4 generally parallel elastic strands spaced generally evenly between the side edges 71 of the cover. More desirably, though, the cover 64 includes at least 6 elastic strands 66, such as the 7 strands shown in FIG. 6. The elastic strands 66 are desirably spaced from neighboring strands by less than about 8 mm, and particularly by from about 3 to about 6 mm from neighboring strands for improved performance.

The individual elastic strands 66 may be identical to one another. Alternatively, however, at least one of the elastic strands 66 has greater elastic power than at least one of the other elastic strands 66. Further, the elastic strands 66 having greater elastic power are desirably located furthest from the point at which the elasticized bumper 202 is bonded to the side margin 38. In the illustrated embodiment, for example, the cover 64 includes 7 elastic strands 66, and 3 of those strands desirably have greater elastic power than the remaining 4 strands. The 3 strands of greater elastic power are desirably located furthest from the adhesive bead 204. Advantageously, this configuration tends to form the undergarment 200 into a "U" shape. Again by way of illustration, a cover 64 may incorporate one set of elastic strands 66 having a decitex of 620 and another set of elastic strands having a decitex of 940. Both sets of strands may be stretched to 270 percent elongation and bonded to the casing layer 65. The set of 940 decitex strands could be positioned on the top portion of the elasticized bumper 202 and the set of 620 decitex strands could be positioned on the side and bottom portions of the bumper.

The elasticized bumpers 202 function to contact the body of the wearer and inhibit lateral movement of liquid. In one embodiment, either the covers 64 or the internal barrier structures 62 comprise a hydrophobic material to inhibit the movement of liquid toward the side edges 28 and 29 of the undergarment 200. To improve conformance to the body of the wearer, the elasticized bumpers 202 desirably possess the height and tension characteristics described above in relation to the elasticized bumpers 60 shown in FIGS. 1–3.

In particularly desirable embodiments, the cover 64 is wrapped about the internal barrier structure 62 but is not bonded to the internal barrier structure. By leaving the cover 64 unadhered to the internal barrier structure 62, the inner surface of the cover is free to slide over the exterior surface of the internal barrier structure, a feature which tends to minimize the formation of large rugosities along the length of the elasticized bumper 202.

Test Methods

Figure 7:
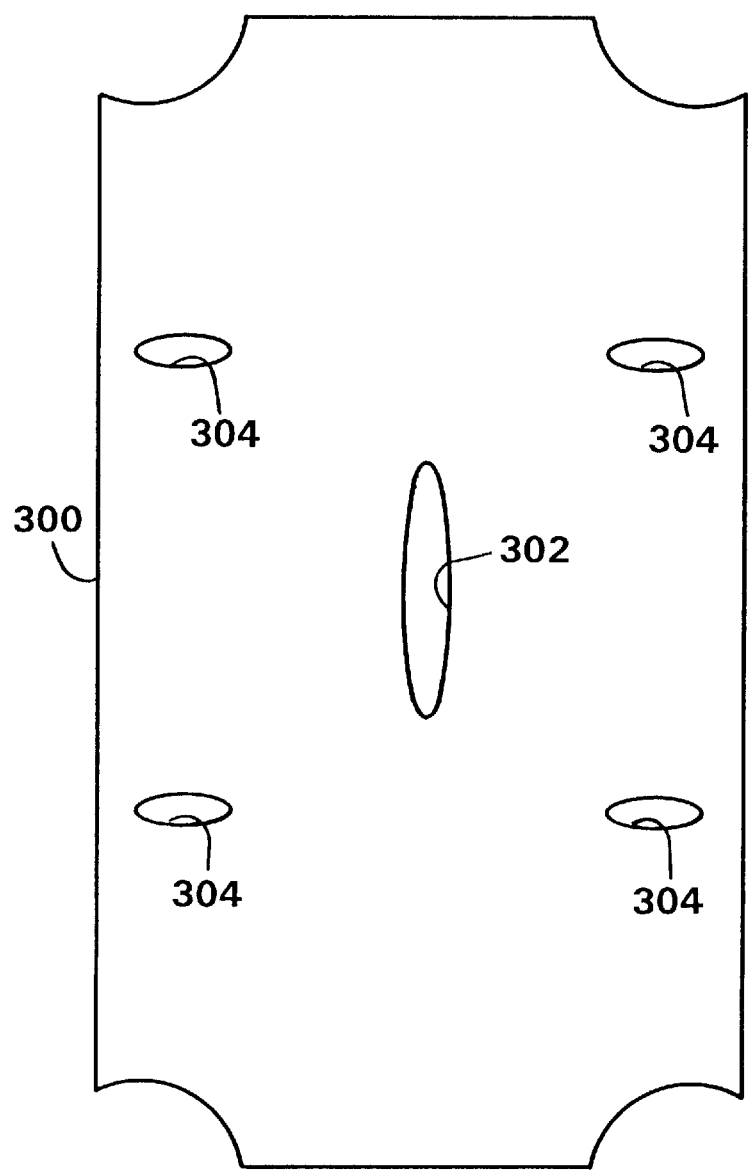
FIG. 7 is a top plan view of a template used in a Product Tension Test.

A suitable technique for determining the side margin tension value of an absorbent article is the following Product Tension Test, which determines the tension of the side margins of the undergarment 20 at a predetermined amount of stretch. The side margins of the undergarment 20 include the elasticized bumpers 60 and 202. The Product Tension Test uses the following equipment and materials:

1. A lightbox mounted in a vertical position with clamps along the top edge.
2. A double clamp weight weighing 1000±5 grams.
3. A template 300 with a centerline reference 302, as illustrated in FIG. 7. The template has a length of 64.4 cm. Along each side of the template, a pair of apertures 304 are centered along the length of the template. The apertures in each pair are separated so that pen marks on a product made through the apertures are separated by 25.4 cm. This distance may need to be modified, for example to 17.78 cm when smaller products such as diapers or training pants are tested. The apertures are spaced from the centerline reference a sufficient distance so that the marks correspond to the lateral location of the elastic strands 66.
4. An elastic tension tester such as a Chatillon DFG2 force gauge available from John Chatillon & Sons Inc. located in New York, N.Y., USA. The force gauge has upper and lower clamps, such as 3 inch Bulldog clamps.
5. An aluminum gage rod measuring 20.3 cm (8 inches) long. The length may be adjusted to 16 cm for smaller products as noted above.
6. Pen with black ink.
7. Weights for calibration, 50, 100, 200, 500 grams, traceable to the National Bureau of Standards (NBS).
8. Scissors
9. Ruler A garment should be tested no sooner than 4 hours after it is produced. The garment to be tested is conditioned in a standard-condition atmosphere of 23±1° C. (73.4±1.8° F.) temperature and 50±2% relative humidity for 4 hours. The equipment is set up in the following manner:

1. Turn on the Chatillon force gauge and allow 10 minutes for the unit to warm-up.
2. Calibrate the Chatillon force gauge using the calibration weights according to the manufacturer's instructions.
3. While supporting the force gage assembly, loosen the locking knob on the back of the force gage assembly. Position the force gage assembly to give approximately 20.3 cm (16 cm for smaller products) of space between the upper and lower clamps. Retighten the locking knob to hold the force gage assembly in place.
4. Hold the gage rod between the upper and lower clamps. Use the fine adjustment knob located above the force gage to adjust the distance until both clamps just touch the rod.
5. Verify that the units of measure on the force gage is set to kilograms.

If required, push the "zero" button to zero the display.

The test specimens are prepared in the following manner. The garment is centered beneath the lightbox clamps and hung with the moisture barrier 40 against the lightbox. If possible, the clamps are attached to avoid the absorbent structure 42 of the garment. The double clamp weight is attached to the lower end of the garment and gently lowered. Next, the template is centered on the garment and each elasticized bumper 60 or 202 is marked with the pen through the apertures. The procedure is repeated until a total of 5 garments are marked. Each garment has two leg cuff regions so there are a total of 10 test specimens.

Each of the 10 test specimens can then be tested by the following procedure.

1. Cut the side margins from each garment while it is hanging. Use the scissors to make a crosswise cut to the absorbent batt about ½ inch (13 mm) beyond the black ink mark. Cut lengthwise between the elasticized bumper and the absorbent batt extending to ½ inch (13 mm) beyond the black ink mark on the other end of the elasticized bumper. Then make a crosswise cut to free the elasticized bumpers from the garment. If the absorbent batt must be cut to remove the elasticized bumpers, the absorbent batt should be cut to remove as much absorbent material from the test specimen as possible.
2. Wait 30 minutes but no more than 60 minutes from the time of cutting before testing the specimen.
3. Place one end of the specimen into the upper clamp so the black line coincides with the leading edge of the clamp. Take care so a foldover in the liner does not get trapped in the clamp, as this may give erroneously high results.
4. Press the "ZERO" button to tare the weight of the specimen.
5. Unhook the lower slider, raise it up, and place the bottom of the specimen in the lower clamp so the marked line coincides with the leading edge of the clamp. The small reading showing on the display should have no effect on the final value.
6. Gently, lower the "Sample" sleeve over a three second time interval until it touches and latches to the bottom latch.
7. Wait 5 seconds, then check the alignment of the black lines with the clamps. If no slippage has occurred, record the reading on the force gauge. If slippage has occurred, replace the clamps as needed and test a new specimen.

The side margin tension is the average of the 10 measured values.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article, comprising:
    a moisture barrier having longitudinal end edges and longitudinal side edges extending between the end edges;
    a bodyside liner bonded to the moisture barrier;
    an absorbent structure disposed between the bodyside liner and moisture barrier, at least one of the bodyside liner and moisture barrier forming opposite margins which extend beyond the absorbent structure; and
    an elasticized bumper disposed in each of the margins, each of the elasticized bumpers comprising:
        an internal barrier structure; and
        an elasticized cover operatively joined to one of the margins, the elasticized cover encircling the internal barrier structure and being unadhered to the internal barrier structure, and wherein the elasticized cover comprises a plurality of generally parallel elastic strands wherein at least one of the elastic strands has greater elastic power than at least one other elastic strand;
    wherein at least one of the internal barrier structures and the elasticized covers are hydrophobic.

2. The absorbent article of claim 1, wherein the at least one elastic strand with greater elastic power is positioned remote from a point at which the elasticized bumper is attached to the margin.

3. The absorbent article of claim 1, wherein each of the elasticized covers comprise a pair of casing layers and at least 4 elastic strands positioned between and operatively joined to the casing layers.

4. The absorbent article of claim 1, wherein the elasticized bumpers have a height dimension of from about 3 to about 25 millimeters.

5. The absorbent article of claim 1, wherein the elastic strands are spaced from neighboring strands by from about 3 to about 6 millimeters.

6. An absorbent article, comprising:
- a moisture barrier having longitudinal end edges and longitudinal side edges extending between the end edges;
- a bodyside liner bonded to the moisture barrier;
- an absorbent structure disposed between the bodyside liner and moisture barrier, at least one of the bodyside liner and moisture barrier forming opposite margins which extend beyond the absorbent structure; and
- an elasticized bumper disposed in each of the margins, each of the elasticized bumpers having a height dimension of from about 3 to about 25 millimeters and comprising:
  - an internal barrier structure; and
  - an elasticized cover operatively joined to one of the margins wherein the elasticized cover comprises a hydrophobic material, the elasticized cover encircling the internal barrier structure and being unadhered to the internal barrier structure and wherein the elasticized covers comprise a plurality of generally parallel elastic strands wherein at least one of the elastic strands has greater elastic power than at least one other elastic strand;

wherein at least one of the internal barrier structures and the elasticized covers are hydrophobic.

7. The absorbent article of claim 6, wherein the at least one elastic strand with greater elastic power is positioned remote from a point at which the elasticized bumper is attached to the margin.

8. The absorbent article of claim 6, wherein each of the elasticized covers comprises at least one casing layer and at least 4 elastic strands operatively joined to the casing layer.

9. The absorbent article of claim 6, wherein the internal barrier structures comprise a hydrophobic material.

* * * * *